(12) United States Patent
Copeland et al.

(10) Patent No.: US 9,168,031 B2
(45) Date of Patent: Oct. 27, 2015

(54) EXPANDABLE THORACIC ACCESS PORT

(71) Applicant: Covidien LP, Mansfield, MA (US)

(72) Inventors: Thomas John Hector Copeland, Hertfordshire (GB); Cormac O'Prey, Hertfordshire (GB); Rebecca Ann Wilkins, Hertfordshire (GB); Daniel Leonard Fuller, Suffolk (GB); Stephen Brown, Hertfordshire (GB); Christopher John Silk, Cambridgeshire (GB); Trevor Beckett, Cambridge (GB)

(73) Assignee: Covidien LP, Mansfield, MA (US)

( * ) Notice: Subject to any disclaimer, the term of this patent is extended or adjusted under 35 U.S.C. 154(b) by 202 days.

(21) Appl. No.: 14/067,393

(22) Filed: Oct. 30, 2013

(65) Prior Publication Data

US 2014/0058207 A1 Feb. 27, 2014

Related U.S. Application Data

(62) Division of application No. 13/166,878, filed on Jun. 23, 2011, now Pat. No. 8,597,180.

(60) Provisional application No. 61/372,939, filed on Aug. 12, 2010.

(51) Int. Cl.
*A61B 17/02* (2006.01)
*A61B 17/34* (2006.01)

(52) U.S. Cl.
CPC ......... *A61B 17/0218* (2013.01); *A61B 17/3423* (2013.01); *A61B 17/3431* (2013.01);
(Continued)

(58) Field of Classification Search
CPC ........... A61B 17/0218; A61B 17/3423; A61B 2017/3427; A61B 17/0293
See application file for complete search history.

(56) References Cited

U.S. PATENT DOCUMENTS 1,780,912 A  11/1930  Gau
1,810,466 A   6/1931  Deutsch
(Continued)

FOREIGN PATENT DOCUMENTS

DE         10001695       2/2001
DE      102009014527      9/2010
(Continued)

OTHER PUBLICATIONS

EP Search Report 11 25 0163 dated Jul. 6, 2011.
(Continued)

*Primary Examiner* — Christian Sevilla

(57) ABSTRACT

A surgical access assembly for positioning within an opening in tissue including an outer member positionable outside a patient and defining an opening therein to receive a surgical instrument. The outer member has a first portion and a second portion wherein at least one of the first and second portions is movable with respect to the other portion. The assembly also includes an inner member positionable within a patient and a flexible member extending between the inner member and outer member, wherein movement of one of the first and second portions of the outer member adjusts tension on the flexible member to retract tissue. A locking mechanism locks the outer member in a plurality of select expanded positions. The locking mechanism includes first engagement structure on the first portion engageable with the second portion and a slidable member movable to a locking position to retain the first and second portions in the select expanded position.

17 Claims, 9 Drawing Sheets

(52) U.S. Cl.
CPC ..... *A61B17/3439* (2013.01); *A61B 2017/0225* (2013.01); *A61B 2017/3427* (2013.01); *A61B 2017/3488* (2013.01)

(56) References Cited

U.S. PATENT DOCUMENTS

| | | | |
|---|---|---|---|
| 2,313,164 A | 3/1943 | Nelson | |
| 2,541,516 A | 2/1951 | Ivory et al. | |
| 2,812,758 A | 11/1957 | Blumenschein | |
| 2,893,378 A * | 7/1959 | Cooper | 600/233 |
| 3,782,370 A | 1/1974 | McDonald | |
| 3,807,393 A | 4/1974 | McDonald | |
| 3,965,890 A | 6/1976 | Gauthier | |
| 4,130,113 A | 12/1978 | Graham | |
| 4,263,899 A | 4/1981 | Burgin | |
| 4,337,762 A * | 7/1982 | Gauthier | 600/234 |
| 4,553,537 A | 11/1985 | Rosenberg | |
| 4,924,857 A * | 5/1990 | Mahmoodian | 600/220 |
| 5,007,900 A | 4/1991 | Picha et al. | |
| 5,052,374 A | 10/1991 | Alvarez-Jacinto | |
| 5,080,088 A | 1/1992 | LeVahn | |
| 5,125,396 A | 6/1992 | Ray | |
| 5,169,387 A | 12/1992 | Kronner | |
| 5,231,974 A | 8/1993 | Giglio et al. | |
| 5,232,451 A | 8/1993 | Freitas et al. | |
| 5,269,754 A | 12/1993 | Rydell | |
| 5,279,575 A | 1/1994 | Sugarbaker | |
| 5,330,501 A | 7/1994 | Tovey et al. | |
| 5,346,484 A | 9/1994 | Van Lindert | |
| 5,366,478 A * | 11/1994 | Brinkerhoff et al. | 606/213 |
| 5,391,156 A | 2/1995 | Hildwein et al. | |
| 5,437,683 A | 8/1995 | Neumann et al. | |
| 5,445,615 A | 8/1995 | Yoon | |
| 5,460,170 A | 10/1995 | Hammerslag | |
| 5,480,410 A | 1/1996 | Cuschieri | |
| 5,490,843 A | 2/1996 | Hildwein et al. | |
| 5,503,617 A | 4/1996 | Jako | |
| 5,520,610 A * | 5/1996 | Giglio et al. | 600/233 |
| 5,524,644 A * | 6/1996 | Crook | 128/888 |
| 5,556,385 A | 9/1996 | Andersen | |
| 5,562,677 A | 10/1996 | Hildwein et al. | |
| 5,653,705 A | 8/1997 | De la Torre et al. | |
| 5,697,891 A | 12/1997 | Hori | |
| 5,718,725 A * | 2/1998 | Sterman et al. | 623/2.11 |
| 5,728,103 A | 3/1998 | Picha et al. | |
| 5,755,660 A | 5/1998 | Tyagi | |
| 5,755,661 A | 5/1998 | Schwartzman | |
| 5,772,583 A | 6/1998 | Wright et al. | |
| 5,776,110 A | 7/1998 | Guy et al. | |
| 5,779,629 A | 7/1998 | Hohlen | |
| 5,788,630 A | 8/1998 | Furnish | |
| 5,803,921 A | 9/1998 | Bonadio | |
| 5,810,721 A | 9/1998 | Mueller et al. | |
| 5,814,097 A * | 9/1998 | Sterman et al. | 623/2.11 |
| 5,846,193 A | 12/1998 | Wright | |
| 5,849,005 A * | 12/1998 | Garrison et al. | 606/1 |
| 5,875,782 A | 3/1999 | Ferrari et al. | |
| 5,879,291 A | 3/1999 | Kolata et al. | |
| 5,906,577 A | 5/1999 | Beane et al. | |
| 5,908,382 A | 6/1999 | Koros et al. | |
| 5,931,778 A | 8/1999 | Furnish | |
| 5,935,107 A | 8/1999 | Taylor et al. | |
| 5,944,736 A | 8/1999 | Taylor et al. | |
| 5,951,466 A | 9/1999 | Segermark et al. | |
| 5,951,467 A | 9/1999 | Picha et al. | |
| 5,957,835 A | 9/1999 | Anderson et al. | |
| 5,967,972 A | 10/1999 | Santilli et al. | |
| 5,993,385 A | 11/1999 | Johnston et al. | |
| 6,024,736 A | 2/2000 | De la Torre et al. | |
| 6,033,362 A | 3/2000 | Cohn | |
| 6,033,425 A | 3/2000 | Looney et al. | |
| 6,036,641 A | 3/2000 | Taylor et al. | |
| 6,048,309 A * | 4/2000 | Flom et al. | 600/234 |
| 6,063,021 A * | 5/2000 | Hossain et al. | 600/37 |
| 6,074,380 A | 6/2000 | Byrne et al. | |
| 6,113,535 A | 9/2000 | Fox et al. | |
| 6,120,436 A | 9/2000 | Anderson et al. | |
| 6,132,370 A | 10/2000 | Furnish et al. | |
| 6,142,935 A | 11/2000 | Flom et al. | |
| 6,159,231 A | 12/2000 | Looney et al. | |
| 6,162,172 A | 12/2000 | Cosgrove et al. | |
| 6,231,506 B1 | 5/2001 | Hu et al. | |
| 6,254,533 B1 | 7/2001 | Fadem et al. | |
| 6,254,534 B1 | 7/2001 | Butler et al. | |
| 6,270,505 B1 * | 8/2001 | Yoshida et al. | 606/127 |
| 6,277,136 B1 * | 8/2001 | Bonutti | 606/190 |
| 6,283,912 B1 | 9/2001 | Hu et al. | |
| 6,309,349 B1 | 10/2001 | Bertolero | |
| 6,312,377 B1 | 11/2001 | Segermark et al. | |
| 6,331,158 B1 | 12/2001 | Hu et al. | |
| 6,332,468 B1 * | 12/2001 | Benetti | 128/898 |
| 6,354,995 B1 | 3/2002 | Hoftman et al. | |
| 6,361,492 B1 | 3/2002 | Santilli | |
| 6,382,211 B1 | 5/2002 | Crook | |
| 6,443,957 B1 | 9/2002 | Addis | |
| 6,450,983 B1 | 9/2002 | Rambo | |
| 6,458,079 B1 | 10/2002 | Cohn et al. | |
| 6,500,116 B1 | 12/2002 | Knapp | |
| 6,517,563 B1 | 2/2003 | Paolitto et al. | |
| 6,547,725 B1 | 4/2003 | Paolitto et al. | |
| 6,585,442 B2 | 7/2003 | Brei et al. | |
| 6,599,240 B2 | 7/2003 | Puchovsky et al. | |
| 6,599,292 B1 | 7/2003 | Ray | |
| 6,616,605 B2 | 9/2003 | Wright et al. | |
| 6,652,454 B2 | 11/2003 | Hu et al. | |
| 6,723,044 B2 | 4/2004 | Pulford et al. | |
| 6,730,021 B2 | 5/2004 | Vassiliades, Jr. et al. | |
| 6,730,022 B2 | 5/2004 | Martin et al. | |
| 6,746,396 B1 * | 6/2004 | Segermark et al. | 600/233 |
| 6,746,467 B1 | 6/2004 | Taylor et al. | |
| 6,814,078 B2 | 11/2004 | Crook | |
| 6,814,700 B1 | 11/2004 | Mueller et al. | |
| 6,840,951 B2 | 1/2005 | De la Torre et al. | |
| 6,846,287 B2 | 1/2005 | Bonadio et al. | |
| 6,958,037 B2 | 10/2005 | Ewers et al. | |
| 7,033,319 B2 | 4/2006 | Pulford et al. | |
| 7,052,454 B2 | 5/2006 | Taylor | |
| 7,144,368 B2 | 12/2006 | Larson et al. | |
| 7,147,599 B2 | 12/2006 | Phillips et al. | |
| 7,179,225 B2 | 2/2007 | Shluzas et al. | |
| 7,195,592 B2 | 3/2007 | Ravikumar et al. | |
| 7,220,228 B2 | 5/2007 | Hu et al. | |
| 7,226,451 B2 | 6/2007 | Shluzas et al. | |
| 7,229,408 B2 | 6/2007 | Douglas et al. | |
| 7,238,154 B2 | 7/2007 | Ewers et al. | |
| 7,261,688 B2 | 8/2007 | Smith et al. | |
| 7,270,632 B2 | 9/2007 | Santilli | |
| 7,300,399 B2 | 11/2007 | Bonadio et al. | |
| 7,344,495 B2 | 3/2008 | Ravikumar et al. | |
| 7,387,126 B2 | 6/2008 | Cox et al. | |
| 7,393,322 B2 | 7/2008 | Wenchell | |
| 7,473,222 B2 | 1/2009 | Dewey et al. | |
| 7,507,202 B2 | 3/2009 | Schoellhorn | |
| 7,507,235 B2 | 3/2009 | Keogh et al. | |
| 7,537,564 B2 | 5/2009 | Bonadio et al. | |
| 7,540,839 B2 | 6/2009 | Butler et al. | |
| 7,559,893 B2 | 7/2009 | Bonadio et al. | |
| 7,566,302 B2 | 7/2009 | Schwer | |
| 7,585,277 B2 | 9/2009 | Taylor et al. | |
| 7,594,888 B2 | 9/2009 | Raymond et al. | |
| 7,650,887 B2 | 1/2010 | Nguyen et al. | |
| 7,736,306 B2 * | 6/2010 | Brustad et al. | 600/208 |
| 8,043,212 B1 * | 10/2011 | Bae et al. | 600/215 |
| 2001/0002429 A1 | 5/2001 | Hu et al. | |
| 2001/0020121 A1 | 9/2001 | Hu et al. | |
| 2001/0041827 A1 | 11/2001 | Spence et al. | |
| 2002/0004628 A1 | 1/2002 | Hu et al. | |
| 2002/0095139 A1 | 7/2002 | Keogh et al. | |
| 2002/0099269 A1 | 7/2002 | Martin et al. | |
| 2002/0099271 A1 | 7/2002 | Knapp | |
| 2002/0137989 A1 | 9/2002 | Clem et al. | |
| 2003/0032975 A1 * | 2/2003 | Bonutti | 606/192 |
| 2003/0191371 A1 | 10/2003 | Smith et al. | |
| 2004/0002629 A1 * | 1/2004 | Branch et al. | 600/210 |

(56) References Cited

U.S. PATENT DOCUMENTS

| | | |
|---|---|---|
| 2004/0015185 A1* | 1/2004 | Ewers et al. .................. 606/213 |
| 2004/0049099 A1* | 3/2004 | Ewers et al. .................. 600/206 |
| 2004/0054353 A1* | 3/2004 | Taylor ............................... 606/1 |
| 2004/0059192 A1 | 3/2004 | Cartier et al. |
| 2004/0225195 A1 | 11/2004 | Spence et al. |
| 2005/0096508 A1 | 5/2005 | Valentini et al. |
| 2005/0171403 A1 | 8/2005 | Paolitto et al. |
| 2005/0228232 A1 | 10/2005 | Gillinov et al. |
| 2005/0241647 A1* | 11/2005 | Nguyen et al. ................. 128/856 |
| 2005/0267336 A1 | 12/2005 | Bertolero et al. |
| 2005/0283050 A1* | 12/2005 | Gundlapalli et al. .......... 600/208 |
| 2006/0004261 A1 | 1/2006 | Douglas |
| 2006/0030861 A1 | 2/2006 | Simonson et al. |
| 2006/0089537 A1 | 4/2006 | Schoellhorn |
| 2006/0106416 A1* | 5/2006 | Raymond et al. ............. 606/198 |
| 2006/0129165 A1 | 6/2006 | Edoga et al. |
| 2006/0149137 A1* | 7/2006 | Pingleton et al. ............. 600/208 |
| 2006/0149306 A1 | 7/2006 | Hart et al. |
| 2006/0155170 A1 | 7/2006 | Hanson et al. |
| 2006/0247498 A1* | 11/2006 | Bonadio et al. ............... 600/208 |
| 2007/0027364 A1 | 2/2007 | Schwer |
| 2007/0073110 A1 | 3/2007 | Larson et al. |
| 2007/0167980 A1 | 7/2007 | Figulla |
| 2007/0203398 A1* | 8/2007 | Bonadio et al. ............... 600/208 |
| 2007/0260125 A1* | 11/2007 | Strauss et al. ................. 600/219 |
| 2008/0132765 A1* | 6/2008 | Beckman et al. ............. 600/204 |
| 2008/0132766 A1 | 6/2008 | Dant et al. |
| 2008/0146884 A1* | 6/2008 | Beckman et al. ............. 600/208 |
| 2008/0208222 A1* | 8/2008 | Beckman et al. ............. 606/148 |
| 2008/0234550 A1 | 9/2008 | Hawkes et al. |
| 2009/0082631 A1* | 3/2009 | Cronin et al. ................. 600/201 |
| 2009/0105655 A1 | 4/2009 | Desantis |
| 2009/0204067 A1 | 8/2009 | Abu-Halawa |
| 2009/0265941 A1 | 10/2009 | Kurrus |
| 2009/0299148 A1 | 12/2009 | White et al. |
| 2009/0326469 A1 | 12/2009 | Rockrohr |
| 2010/0168522 A1 | 7/2010 | Wenchell |
| 2010/0210916 A1 | 8/2010 | Hu et al. |
| 2010/0234689 A1 | 9/2010 | Wagner et al. |
| 2010/0298646 A1 | 11/2010 | Stellon |
| 2011/0021879 A1 | 1/2011 | Hart et al. |
| 2011/0071473 A1* | 3/2011 | Rogers et al. ............. 604/167.01 |
| 2012/0143009 A1* | 6/2012 | Wilkins et al. ................. 600/206 |
| 2013/0178712 A1* | 7/2013 | Malkowski et al. .......... 600/208 |

FOREIGN PATENT DOCUMENTS

| | | |
|---|---|---|
| EP | 0177177 | 4/1986 |
| EP | 2179699 | 4/2010 |
| EP | 2228014 | 9/2010 |
| EP | 2228024 | 9/2010 |
| EP | 2238931 | 10/2010 |
| EP | 2 422 725 | 2/2012 |
| EP | 2417922 | 2/2012 |
| EP | 2 462 883 | 6/2012 |
| GB | 2275420 | 8/1994 |
| WO | WO95/00197 | 1/1995 |
| WO | WO95/15715 | 6/1995 |
| WO | WO01/08563 | 2/2001 |
| WO | WO03/034908 | 5/2003 |
| WO | WO2005/089655 | 9/2005 |
| WO | WO2010/042913 | 4/2010 |
| WO | WO2010/136805 | 12/2010 |
| WO | WO2011/079374 | 7/2011 |

OTHER PUBLICATIONS

EP Search Report 11 25 0164 dated Aug. 6, 2011.
EP Search Report 11 25 0719 dated Nov. 16, 2011.
EP Search Report 11 18 9987 dated Feb. 15, 2012.
EP Search Report 12160423.5 dated Jun. 25, 2012.
EP Search Report EP 11 19 1403 dated Dec. 11, 2013.
EP Search Report EP 12 15 4733 dated Jan. 14, 2014.

* cited by examiner

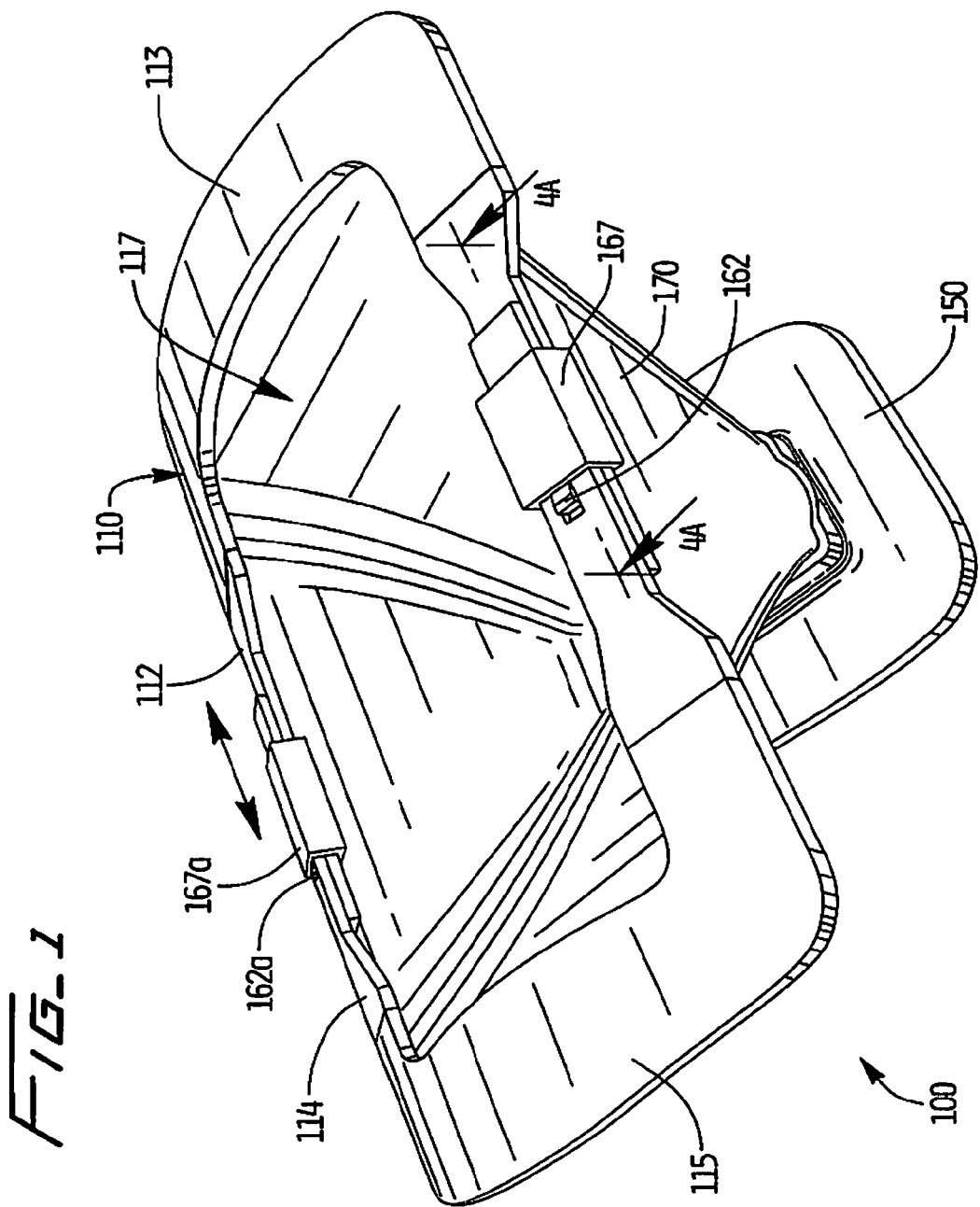

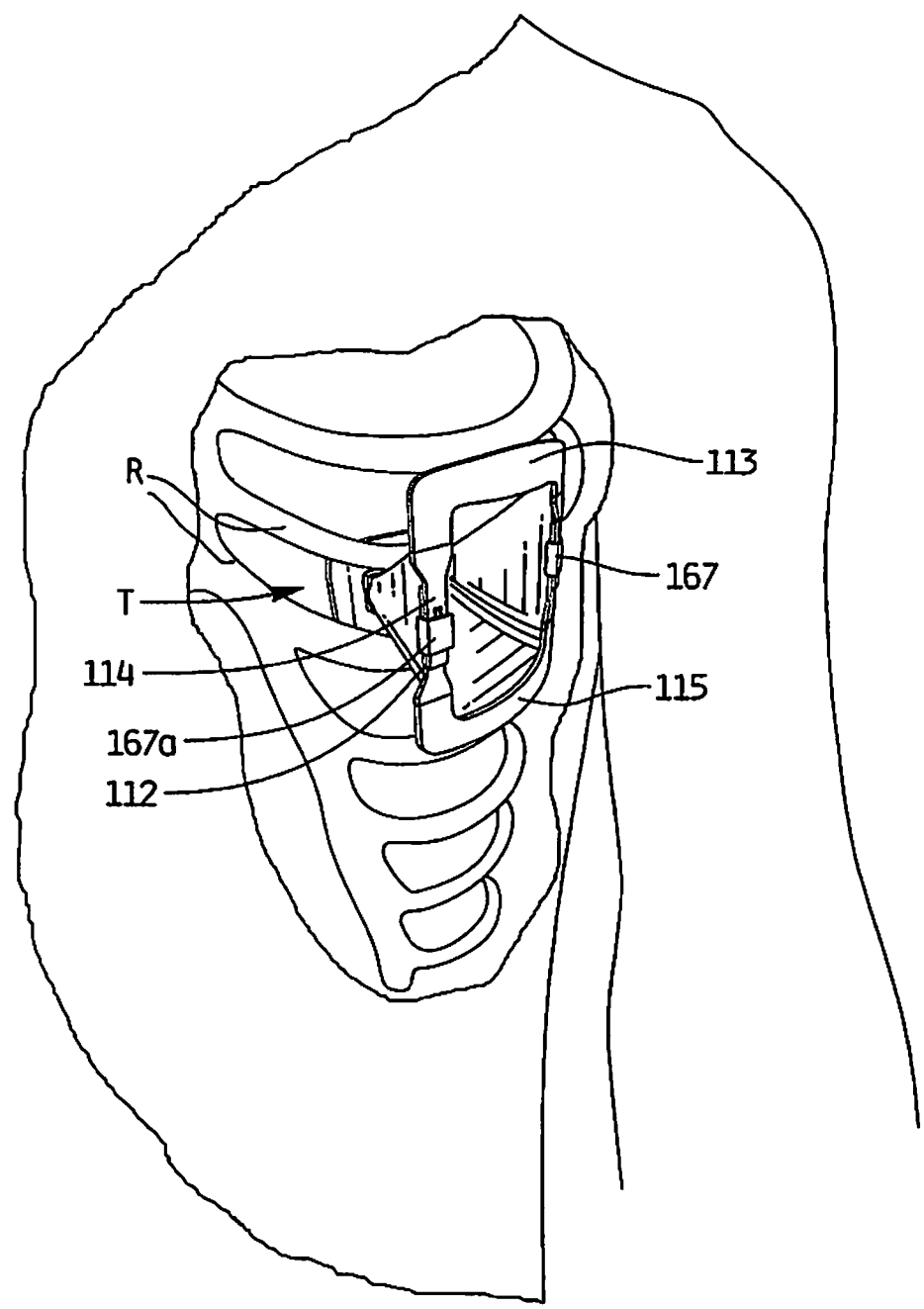

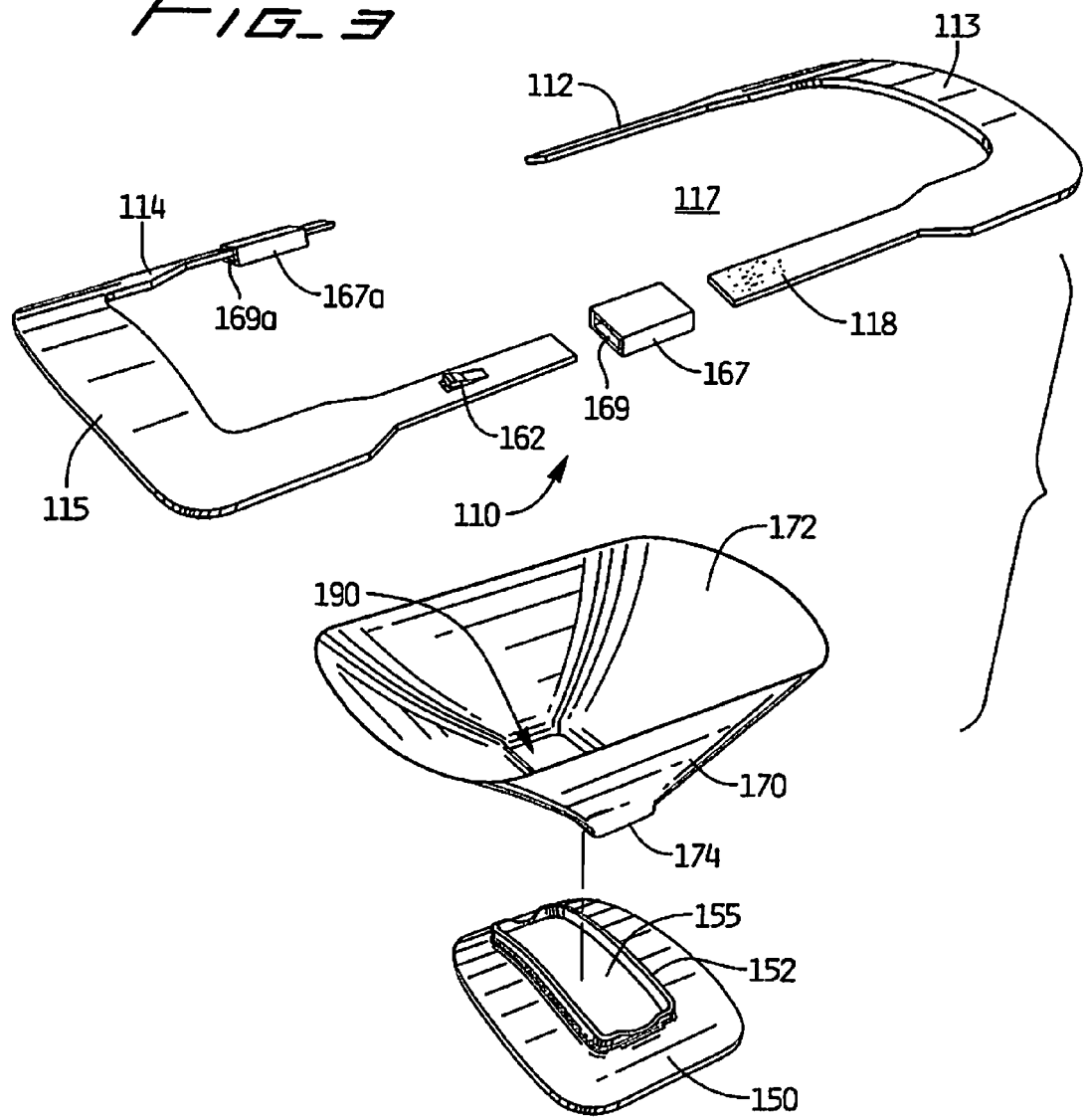

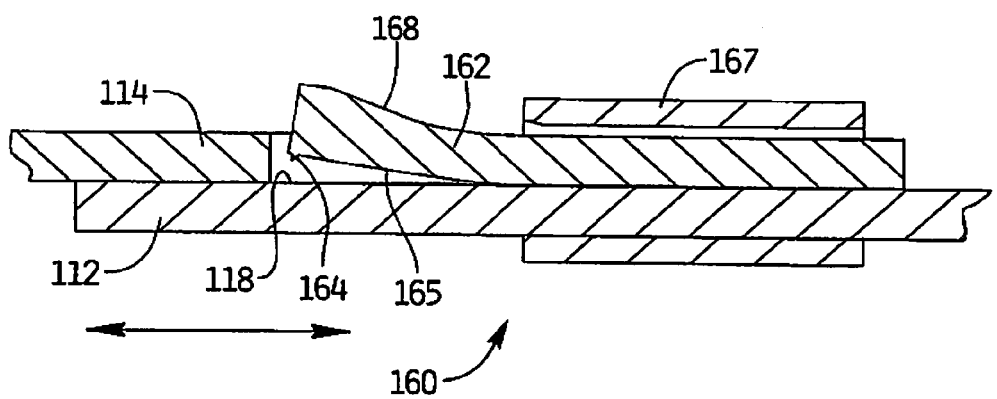
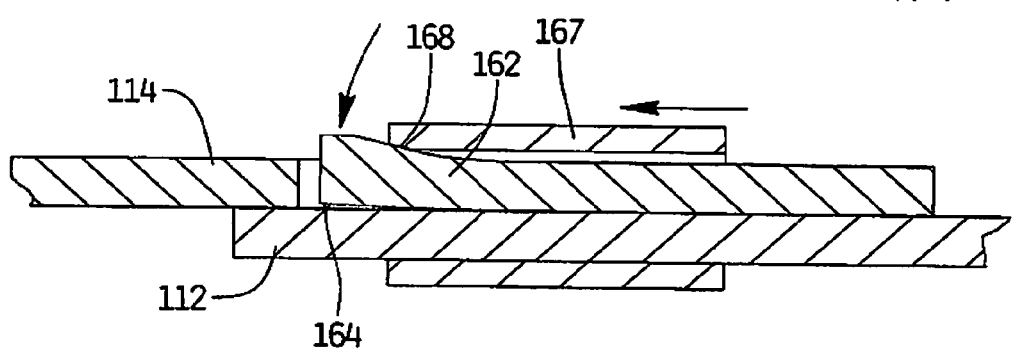
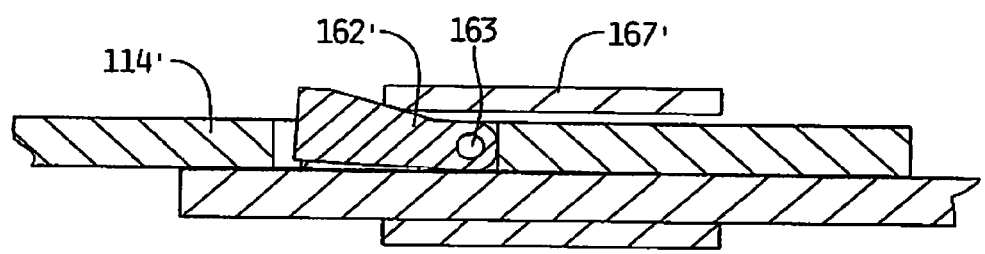

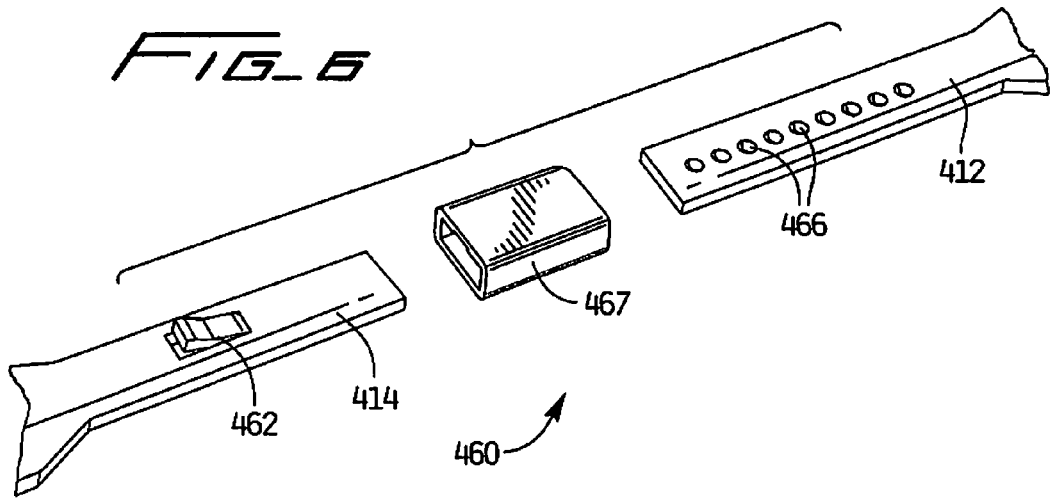
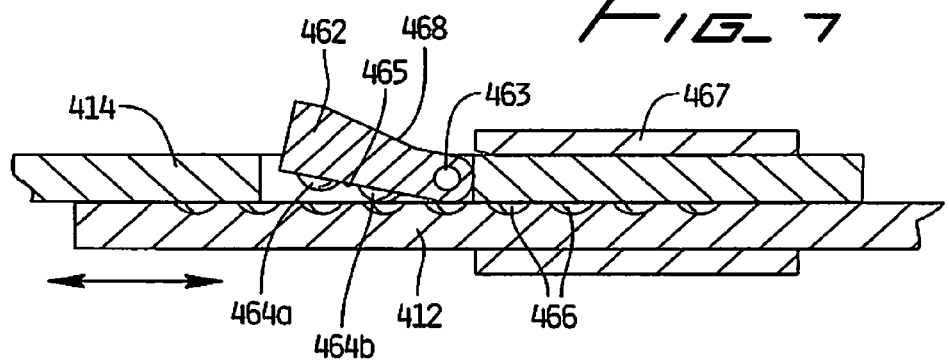
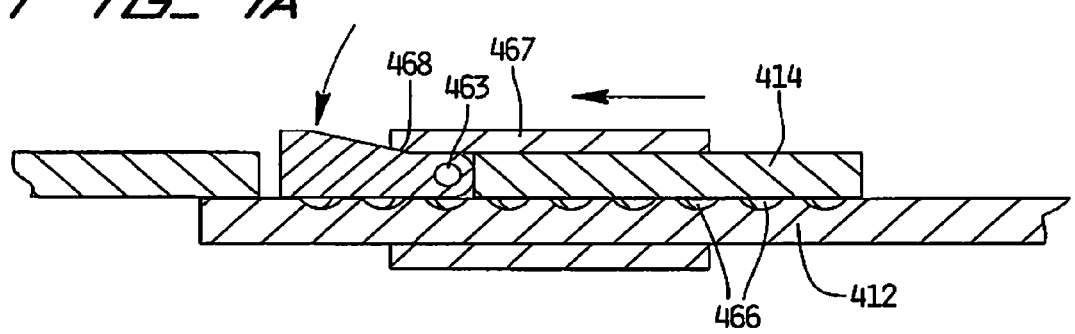

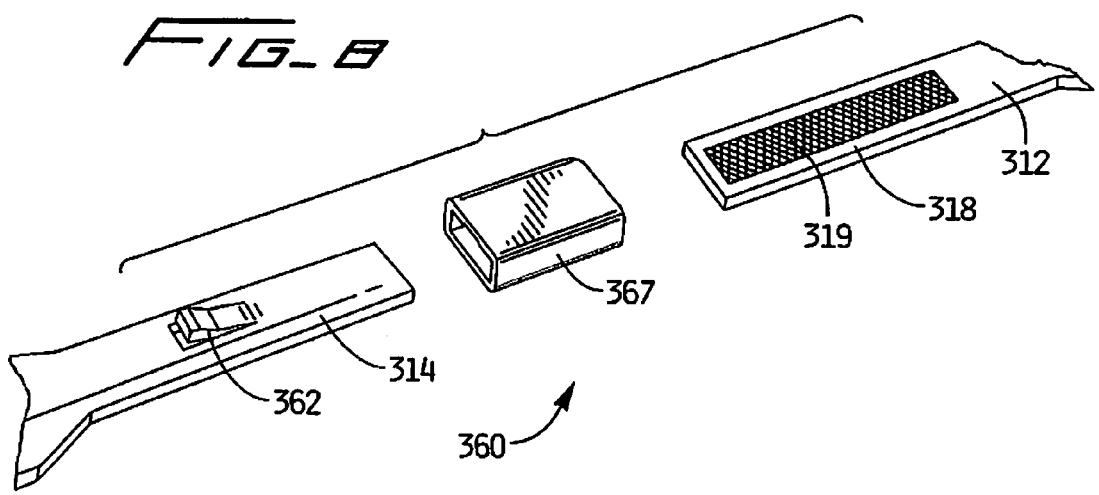
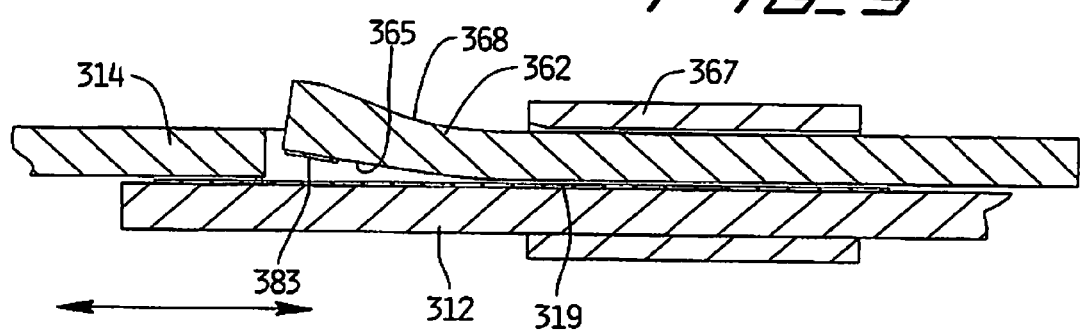
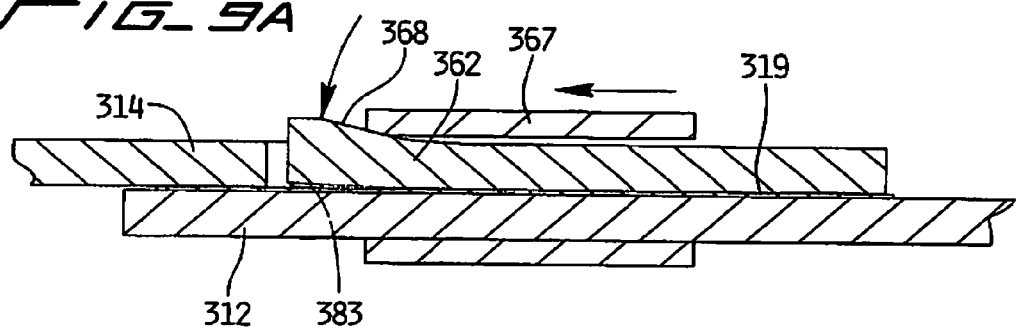

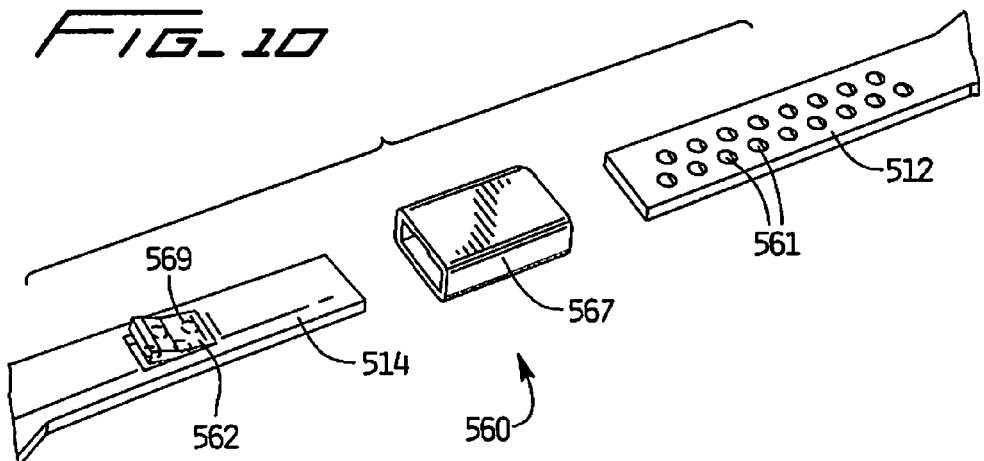
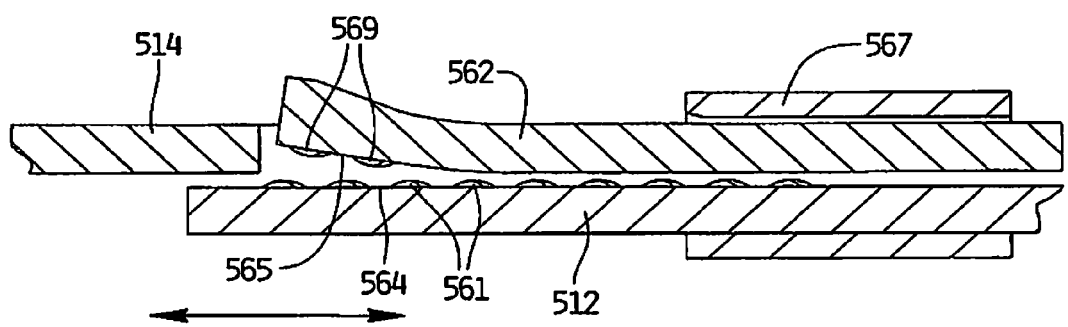
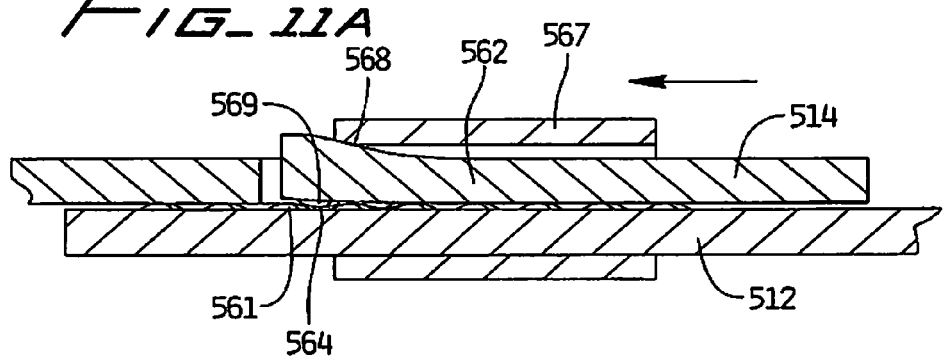

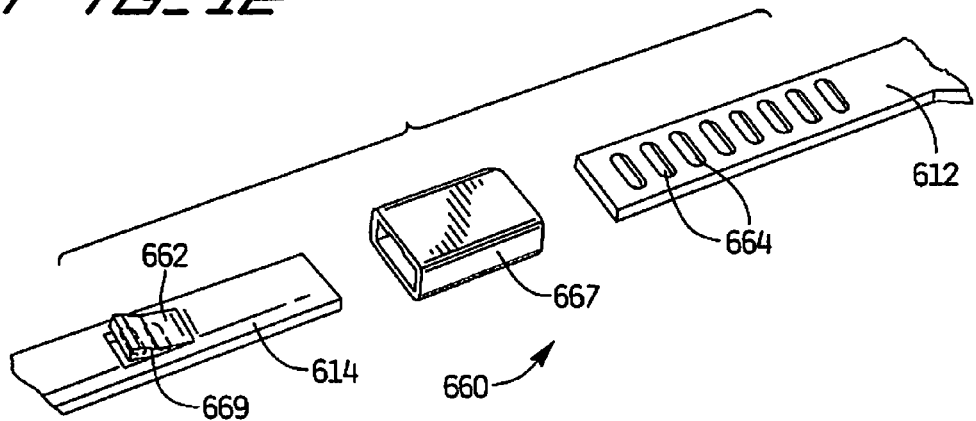
FIG_12
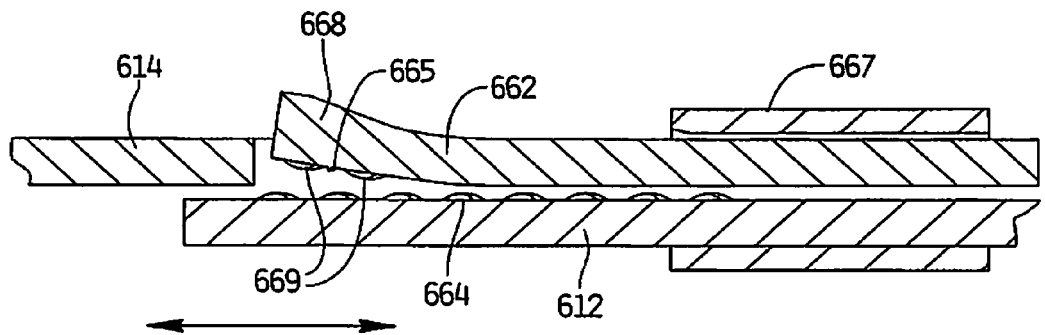
FIG_13
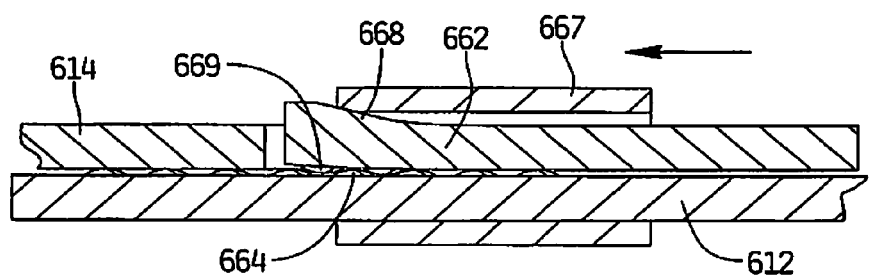
FIG_13A

EXPANDABLE THORACIC ACCESS PORT

CROSS-REFERENCE TO RELATED APPLICATIONS

This application is a division of U.S. patent application Ser. No. 13/166,878, filed on Jun. 23, 2011, which claims the benefit of, and priority to, U.S. Provisional Patent Application Ser. No. 61/372,939, filed on Aug. 12, 2010, now expired, the entire content of each application being incorporated by reference herein.

BACKGROUND

1. Technical Field

The present disclosure relates generally to devices and techniques for performing surgical procedures. More particularly, the present disclosure relates to an expandable access device for minimally invasive surgery.

2. Background of the Related Art

In an effort to reduce trauma and recovery time, many surgical procedures are performed through small openings in the skin, such as an incision or a natural body orifice. For example, these procedures include laparoscopic procedures, which are generally performed within the confines of a patient's abdomen, and thoracic procedures, which are generally performed within a patient's chest cavity.

Specific surgical instruments have been developed for use during such minimally invasive surgical procedures. These surgical instruments typically include an elongated shaft with operative structure positioned at a distal end thereof, such as graspers, clip appliers, specimen retrieval bags, etc.

During minimally invasive procedures, the clinician creates an opening in the patient's body wall, oftentimes by using an obturator or trocar, and thereafter positions an access assembly within the opening. The access assembly includes a passageway extending therethrough to receive one or more of the above-mentioned surgical instruments for positioning within the internal work site, e.g. the body cavity.

During minimally invasive thoracic procedures, an access assembly is generally inserted into a space located between the patient's adjacent ribs that is known as the intercostal space, and then surgical instruments can be inserted into the internal work site through the passageway in the access assembly.

In the interests of facilitating visualization, the introduction of certain surgical instruments, and/or the removal of tissue specimens during minimally invasive thoracic procedures, it may be desirable to spread the tissue adjacent the ribs defining the intercostal space. Additionally, during these procedures, firm, reliable placement of the access assembly is desirable to allow the access assembly to withstand forces that are applied during manipulation of the instrument(s) inserted therethrough. However, reducing patient trauma during the procedure, discomfort during recovery, and the overall recovery time remain issues of importance. Thus, there exists a need for thoracic access ports which minimize post operative patient pain while enabling atraumatic retraction of tissue and which do not restrict access to the body cavity, as well as facilitate retrieval of tissue specimens from the body cavity.

SUMMARY

In accordance with one aspect of the present disclosure, a surgical access assembly for positioning within an opening in tissue is provided. The surgical access assembly comprises an outer member positionable outside a patient and defining an opening therein to receive a surgical instrument therethrough. The outer member includes first and second portions, at least one of the first and second portions movable with respect to the other portion. The access assembly further includes an inner member positionable within a patient and a flexible member extending between the inner member and outer member and operatively associated with the outer member. A locking mechanism locks the outer member in a plurality of select expanded positions, wherein movement of one of the first and second portions adjusts tension on the flexible member to retract tissue. The locking mechanism includes first engagement structure on the first portion engageable with the second portion and a slidable member movable to a locking position to retain the first and second portions in the select expanded position.

In some embodiments, the outer member is substantially rectangular in configuration. The access assembly in some embodiments includes a nerve protecting member extending from the inner member, the nerve protecting member extending in a direction toward the outer member.

In one embodiment, the engagement structure includes a substantially rigid projecting member having a sharp tip embeddable within a softer material. In an alternate embodiment, the engagement structure comprises a first textured surface on the first portion engageable with a second textured surface on the second portion. In another alternate embodiment, the engagement structure includes a first set of projections formed on the first portion and engageable with a second set of projections formed on the second portion, and the second set of projections can be out of phase with the first set of projections. In another alternate embodiment, the engagement structure includes a row of raised bars.

In some embodiments, the engagement structure is biased to a non-engaging position and the slidable member moves the engagement structure to an engaged position.

In some embodiments, the slidable member of the locking mechanism includes first and second collars connected by a bridge.

In some embodiments, a pivoting arm is provided having a detent positioned thereon, the slidable member biasing the pivoting arm to an engaged position when the slidable member is moved to the locking position.

In another aspect of the present disclosure, a surgical access assembly for positioning within an opening in tissue is provided. The surgical access assembly comprises an outer member having an opening dimensioned and configured to receive a surgical instrument therethrough and including first and second portions, at least one of the first and second portions being movable relative to the second portion. The first portion has a first engagement structure and the second portion has a second engagement structure. A flexible member extends distally with respect to the outer member, the flexible member being spread upon movement of the first portion away from the second portion to retract soft tissue adjacent the opening in tissue. A locking or retention mechanism retains the first and second portions of the outer member in a plurality of spread positions, the locking mechanism having a first position wherein the first engagement structure is out of locking engagement with the locking second engagement structure and a second position wherein the first engagement structure is in locking engagement with the second engagement structure to retain the first and second portions in a select spread position.

In some embodiments, the first engagement structure extends from a pivoting arm normally biased to a non-engaged position.

In some embodiments, the locking mechanism includes a member positionable over the first and second engagement structures to lock the first and second portions in a select spread position.

In some embodiments, the first engagement structure is positioned on first and second sides of the first portion and the second engagement structure is positioned on third and fourth sides of the second portion, and the locking mechanism includes first and second collars joined by a bridge member, the first collar slidable over the engagement structures on the first and third sides and the second collar slidable over the engagement structures on the second and fourth sides.

The present disclosure also provides in another aspect a method of accessing an internal cavity of a patient comprising the steps of:

forming an opening in a patient's tissue;
providing an access assembly including:
an outer member positionable outside a patient and defining an opening therein, the outer member including first and second portions, the first portion movable with respect to the second portion to adjust the opening, the opening dimensioned to receive a surgical instrument therethrough;
an inner member positionable within a patient; and
a flexible member extending between the inner member and outer member and operatively associated with the outer member, the flexible member having a passageway to receive a surgical instrument therethrough, wherein movement of the first portion of the outer member adjusts a tension on the flexible member;
inserting the inner member of the access assembly through the opening in tissue within an intercostal space of the patient and the flexible member extending proximally through the opening in tissue;
moving the first portion of the outer member to a select unlocked spread position to enlarge the opening in tissue and the passageway through the flexible member; and
subsequently moving a locking member to lock the first portion in the select spread position.

The method may further comprise the step of introducing at least one of surgical instrumentation and tissue specimen through the passageway and opening in the tissue. In preferred embodiments, the first and second portions frictionally engage when the locking member is moved to lock the first portion.

The method can further include the step of folding the inner member for insertion within the intercostal space into an internal cavity.

BRIEF DESCRIPTION OF THE DRAWINGS

Various embodiments of the subject access port are described herein with reference to the drawings wherein:

FIG. 1 is a perspective view of one embodiment of the access port of the present disclosure;

FIG. 2 is front view illustrating a patient's skeletal structure with the surgical access port of FIG. 1 positioned within the intercostal space defined between adjacent ribs in accordance with the present disclosure;

FIG. 3 is an exploded perspective view of the access port of FIG. 1;

FIG. 4 is a cross-sectional view of one embodiment of the locking mechanism of the present disclosure shown in the unlocked position;

FIG. 4A is a cross-sectional view similar to FIG. 4 showing the locking mechanism in the locked position (taken along line 4A-4A of FIG. 1);

FIG. 5 is a view similar to FIG. 4 showing an alternate embodiment of the locking mechanism;

FIG. 6 is an exploded perspective view of another alternate embodiment of the locking mechanism of the present disclosure;

FIG. 7 is a cross-sectional view of the locking mechanism of FIG. 6 shown in the unlocked position;

FIG. 7A is a cross-sectional view similar to FIG. 7 showing the locking mechanism in the locked position;

FIG. 8 is an exploded perspective view of another alternate embodiment of the locking mechanism of the present disclosure;

FIG. 9 is a cross-sectional view of the locking mechanism of FIG. 8 shown in the unlocked position;

FIG. 9A is a cross-sectional view similar to FIG. 9 showing the locking mechanism in the locked position;

FIG. 10 is an exploded perspective view of yet another alternate embodiment of the locking mechanism of the present disclosure;

FIG. 11 is a cross-sectional view of the locking mechanism of FIG. 10 shown in the unlocked position;

FIG. 11A is a cross-sectional view similar to FIG. 11 showing the locking mechanism in the locked position;

FIG. 12 is an exploded perspective view of another alternate embodiment of the locking mechanism of the present disclosure;

FIG. 13 is a cross-sectional view of the locking mechanism of FIG. 12 shown in the unlocked position; and FIG. 13A is a cross-sectional view similar to FIG. 13 showing the locking mechanism in the locked position.

DETAILED DESCRIPTION

Figure 1A:
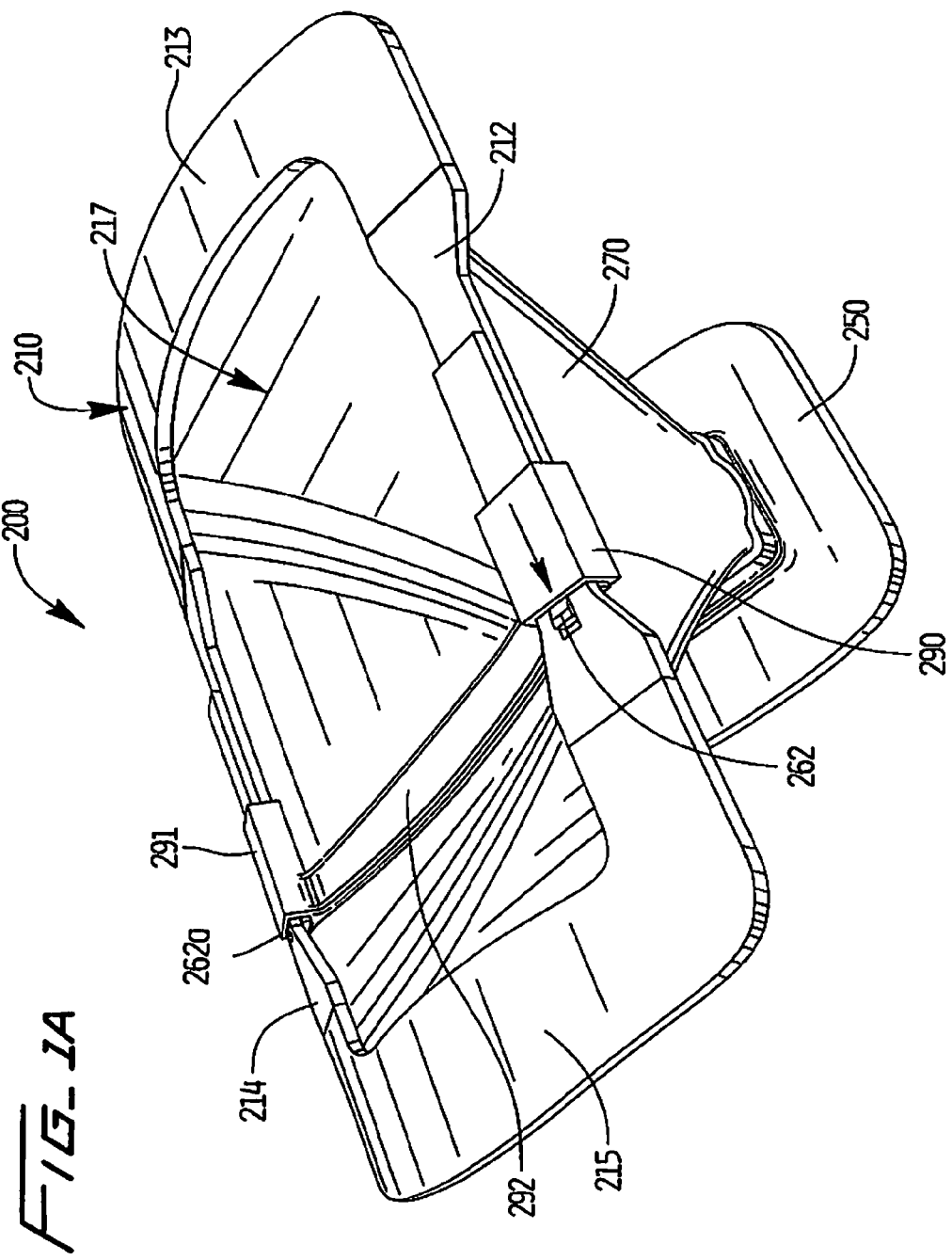
FIG. 1A is a perspective view of an alternate embodiment of the access port of the present disclosure.

Various embodiments of the presently disclosed access assembly, or access port, and methods of using the same, will now be described in detail with reference to the drawings wherein like references numerals identify similar or identical elements. In the drawings, and in the following description, the term "proximal" refers to the end of the access port, or component thereof, that is closer to the clinician and the term "distal" refers to the end that is further from the clinician, as is traditional and conventional in the art. It should be also be understood that the term "minimally invasive procedure" is intended to include surgical procedures through small openings/incisions performed within a confined space such as the thoracic cavity. Note the use of the terms upper and lower are with reference to the orientation shown in the Figures.

Referring now to FIGS. 1 and 3, a first embodiment of the presently disclosed surgical access port, generally identified by the reference numeral 100, is depicted as a thoracic port 100 that is configured and dimensioned for insertion into the intercostal space located between the adjacent ribs "R" (FIG. 2) of a patient in order to allow for the insertion and manipulation of one or more surgical instruments within the thoracic cavity. However, it is also envisioned that access port 100 may be configured and dimensioned to provide access to a variety of other internal body cavities and/or tissues. Access port 100 may be formed from any suitable biocompatible material of strength suitable for the purpose described herein, including, but not being limited to, polymeric materials.

The access port 100 is configured and dimensioned to extend into a body cavity, e.g., the thoracic cavity "T" (FIG. 2), through the intercostal space, and generally includes an outer or proximal frame or member 110 having first and second portions 112, 114. A flexible member, e.g. membrane 170, is coupled to frame 110 and extends distally therefrom. The distal end of the flexible member 170 is attached to an inner or distal frame (or member) 150. The outer frame 110 is movable between various spread positions to widen the passageway for insertion of instrumentation. More specifically, portions 112 and 114 of frame 110 are relatively slidable to increase the distance between respective end walls 113, 115, and to increase the size of the opening 117 in the frame 110. The sliding of portions 112 and 114 applies tension to the flexible member 170 to retract tissue adjacent the incision in the patient to widen the access opening in the manner described below. It should be appreciated that although as described below both the first and second portions 112, 114 are slidable, it is also contemplated that only the first portion 112 (or lower portion as viewed in the orientation of FIG. 1) is slidable with respect to the second (upper) portion 114, or that only the second portion 114 (the upper portion as viewed in the orientation of FIG. 1) is slidable with respect to the first (lower) portion 112.

As shown, the outer frame 110 is substantially rectangular in shape with a substantially rectangular opening. As can be appreciated, other shape frames and openings are also contemplated. Note also that preferably the shape is elongated, e.g. has a length greater than its width.

Inner member 150 has an elongated opening 155 therethrough for passage of surgical instrumentation. The member 150 also has a nerve protecting wall or lip 152 extending along the opening 155, and preferably substantially surrounding the opening. Lip 152 extends upwardly toward outer frame 110. The member 150 is preferably composed of a substantially rigid material to provide anchoring of the access port while of sufficient flexibility to be bent or reconfigured for insertion as described below.

Flexible membrane 170 is generally funnel shaped, is coupled at its distal end 174 to lip 152 of inner member 150 and extends proximally therefrom. Proximal end 172 of flexible membrane 170 is coupled to end walls 113, 115 to isolate tissue surrounding access port 100 from the passageway 190 extending therethrough, thus reducing the risk of tissue damage and/or infection during the surgical procedure. It can be attached by various methods such as welding or gluing. It is envisioned that flexible membrane 170 is configured for soft tissue retraction. It is also envisioned that flexible membrane 170 can be of sufficient elasticity to permit retraction of a wide range of tissue thicknesses since there may be a wide range of tissue thicknesses among different patients. It is also envisioned that flexible membrane 170 is of sufficient strength to prevent accidental tearing and/or puncture by surgical instrumentation inserted through access port 100. Additionally, it is envisioned that flexible membrane 170 be made from a bio-compatible material to reduce the incidents of adverse reaction by a patient upon contact with the patient's tissue. Flexible membrane 170 may also be made of a transparent material to allow the surgeon to better visualize the surgical site and surrounding tissue.

Outer frame 110 is preferably sufficiently rigid to retain membrane 170 in a tensioned configuration. As frame 110 is expanded (spread) in the direction of the arrow of FIG. 1, membrane 170 is tensioned and stretched radially outwardly to retract tissue and/or to expand the passageway 190 extending through membrane 170.

Several alternate embodiments of a locking mechanism for outer frame 110 are disclosed herein. Each of the locking mechanisms includes a first engagement structure on the first portion and a second engagement structure on the second portion of the outer frame and a slidable locking member which locks the first and second portions in the selected spread position. In this manner, the first and second portions of the outer frame are moved apart to a desired spread position to expand and stretch the flexible membrane 170 and then retained or locked in the select position. Such engagement structure is preferably positioned on both sides of the frame 110.

The locking mechanism of FIG. 4 will first be described. This locking mechanism is shown in conjunction with FIG. 1, it being understood that the various locking mechanisms described herein can be utilized with the access port of FIG. 1 or the access port of FIG. 1A. Note that preferably there are two locking mechanisms in each of the locking mechanism embodiments disclosed herein, one on each side of the frame 110 as shown in FIGS. 1 and 3 and described below.

In the embodiment of FIG. 4, locking mechanism 160 includes a first pivoting locking arm 162 positioned on a first side of the second portion 114. The arm 162 can be formed integrally with the second portion, e.g. similar to an integral tab formed for example by a cutout in the second portion 114. Alternatively, the arm 162 can be a separate element attached to the second portion such as shown in FIG. 5 where pivoting arm 162' is attached by pin 163 to frame portion 114' and cammed by sliding collar 167'. Other attachment methods can also be utilized.

A second pivoting locking arm 162a (see FIG. 1) identical to locking arm 162 is provided on the opposing side of portion 114 and functions in the same manner as locking arm 162.

The pivoting arm 162 (and 162a) is preferably biased to a position away from the second portion 112 so in its normal position its lower surface 165 does not engage the first portion 112. That is, in the orientation of FIGS. 1 and 4, it is spring biased upwardly. Arm 162 includes a ramped surface 168 for engagement by a locking collar described below. It is also contemplated that in its normal position the lower surface of the arm 162 (and 162a) it can be slightly engaged with the first portion 112, but not sufficiently engaged to lock the first and second portions 112, 114 or restrict movement.

In the FIG. 4 embodiment, a sharp pointed tip 164, preferably composed of metal, extends from lower surface 165 of arm 162 to provide an engagement structure. The lower portion 112 of frame 110 is composed of a material, at least on its upper surface 118, to enable reception of the tip 164. That is, when pivoting arm 162 is forced by sliding collar member 167 into engagement with lower portion 112, tip 164 digs into the soft material engagement structure on upper surface 118 and becomes embedded therein, thus helping to retain the two engagement structures. This restricts movement of the upper and lower portions 114, 112. Thus, in use, once the desired spread position of the lower portion 112 and upper portion 114 is achieved to tension membrane 170 and retract tissue, sliding member or collar 167 is slid in the direction of the arrow to pivot arm 162 into engagement with lower portion 112. This locking position of arm 162 is shown in FIG. 4A. Locking arm 162a preferably has an identical sharp pointed tip and functions in the identical fashion as locking arm 162, i.e. embeds in the soft material of lower portion 112 when collar 167a, identical to collar 167, is slid over arm 162a. The collars 167, 167a maintain the engagement structures in their locking position.

In a preferred embodiment, the first and second collars 167, 167a are substantially identical and each have an opening 169, 169a for sliding reception of the frame 114. Other configurations of collars then that shown in the various embodiments herein are also contemplated as long as it achieves its function of movement to clamp the respective pivoting arm 162, 162a into locking arrangement.

In the embodiment of FIG. 1, two separate collars are provided which are independently movable. However, it is also contemplated that the two collars can be connected such that they both can be moved simultaneously and in a single movement by the surgeon. This variation is shown in FIG. 1A. The components of FIG. 1A are substantially identical to those of FIG. 1, except for the collars, and have the same reference numerals except are numbered in the "200 series." Therefore, access port 200 has an outer frame or member 210 with pivoting locking arms 262, 262a, a flexible membrane 270 and an inner frame or member 250, etc. For clarity and brevity, further details of these components are not described or designated in FIG. 1A since they are the same as those of FIG. 1.

The difference between FIG. 1 and FIG. 1A is the slidable locking collar 290. As shown, first slidable locking collar 290 is positioned on one side of frame 210 and a second slidable locking collar 291 is positioned on a second side of frame 210. A bridge 292 connects the two collars 290, 291 and extends across the opening 217 in frame 210, preferably spaced from the center of the opening 217 so as not to interfere with the passage of surgical instrumentation therethrough. After the first and second portions 212, 214 of frame 210 are spread to the select position in the same manner as in the embodiments of FIG. 1 to tension membrane 270, the bridge can be moved (pulled toward wall 215 in the embodiment of FIG. 1A) to move the collars 290, 291 in the direction of the arrow to cam the pivoting arms 262, 262a downwardly into engagement with the upper surface of lower portion 212 to retain the portions 212, 214 in the select position in the same manner as in FIG. 1. It should be appreciated that any of the locking mechanisms and engagement structures disclosed herein can be utilized with the bridged collars of FIG. 1A.

It should also be appreciated that although the collars 290, 291 are pulled to lock portions 112, 114 because of their initial position (between arms 262, 262a and wall 213), it is also contemplated that in their initial position the collars can be on the other side of pivoting arms 262, 262a, i.e. closer to the wall 215. In this version, the bridge 291 would be pushed in a direction away from wall 215 to ride over and cam arms 262, 262a into engagement with lower portion 212 to lock the frame portions 212, 214 in a select position.

Turning now to other alternate embodiments, and turning first to FIGS. 8-9, the access port differs from access port 100 of FIG. 1 in the engagement structures of the locking mechanisms. Otherwise, the ports are identical.

Pivoting locking arm 362 has a bottom surface 365 with an engagement structure in the form of a textured surface 383, preferably molded thereon. A second engagement structure in the form of a high friction textured surface 319 is preferably molded onto the top surface 318 of lower portion 314 (as viewed in the orientation of FIG. 8). Other methods of providing a textured surface are also contemplated. Different types of textured surfaces can be utilized such as beads, ridges, domes and/or points which interlock with a textured surface of lower portion 312. A second locking arm identical to locking arm 362 is provided on the other side of upper portion 314 and operates in the same fashion. Sliding collar 367 contacts ramped surface 368 of pivoting arm 362 to bias textured surface 383 into locking engagement with textured surface 319. Another sliding collar identical to collar 367 contacts the other locking arm in the same manner. This movement of the collars locks the upper and lower portions 314, 312 in the same manner as the collars 167, 167a of FIG. 1.

In the alternate embodiment of FIG. 6, the access port differs from access port 100 of FIG. 1 in the engagement structures. Otherwise, the ports are identical. Locking mechanism 460 includes a first pivoting locking arm 462 and a second pivoting locking arm (not shown), each biased away from the lower frame portion 412 (as viewed in the orientation of FIG. 6) in the same manner as described above with respect to the locking arms 162, 162a of FIG. 1. As in the embodiment of FIG. 4, as well as the other embodiments herein, the first pivoting arm 462 (and second arm) can be a separate component attached to the upper frame portion 414 by a pin 463 as shown or by other methods, or alternately formed integrally with the frame 414.

Locking arm 462 includes a bottom surface 465 with two detents 464a, 464b. These detents 464a, 464b are configured and dimensioned to be received in locking engagement within two of the plurality of recesses 466 (only a few are labeled for clarity) in the bottom portion 412. Note the number of recesses 466 preferably exceeds the number of detents 464a, 464b to enable locking in a number of different select positions of the frame portion 412, 414. It should be appreciated that the number of detents and recesses can be different than that shown.

A second locking arm (not shown), identical to locking arm 462, is positioned on the other side of the second (upper) portion 414. As with locking arm 462, the second locking arm has two (or more) detents engageable with two of the recesses on a second side of the second portion 412, depending on the relative position of the first and second portions.

A locking member in the form of a sliding collar 467 is slid over the ramped surface 468 of arm 462 to force it downwardly against its normal bias into engagement with the recesses 466. Thus, in use, after spreading the lower and upper portions 412, 414 to the desired position to tension the membrane and retract tissue around the incision in the same manner as in the embodiment of FIG. 1 (and/or FIG. 1A), the surgeon slides first collar 467 (and the second collar) over the respective pivoting arm 462, resulting in engagement of the decent engagement structure with the recess engagement structure. The second sliding collar operates in the same fashion as collar 467 to pivot the respective arm to provide engagement of the detents of this arm with the underlying recesses. Note if at the desired spread position the detents are not in exact alignment with a recess, the upper and/or lower portion 414, 412 can slide slightly until the detents on both sides of the upper portion 414 are aligned with the recesses on the lower portion 412. As noted above, with the exception of the locking mechanism 460, this embodiment is identical to that of FIG. 1.

FIGS. 10 and 11 illustrate an alternate embodiment of the locking mechanism, designated generally by reference numeral 560 which can be utilized with the access ports of FIGS. 1 and 1A. That is, the access port of FIG. 10 is identical to the access port 100 of FIG. 1 except for the locking mechanism. More specifically, locking mechanism 560 has a plurality of projections, e.g. domes or balls 561 on an upper surface of the lower portion 512 and a plurality of projections, e.g. domes or balls 569, on the lower surface 565 of the pivoting locking arm 562. Although the arm 562 is shown integral, as in the other embodiments disclosed herein, it could alternatively be a separate component attached to the upper portion. Only a few of the domes/balls are labeled for clarity.

In the illustrated embodiment, two rows of domes 569 are positioned on pivoting arm 562 of frame portion 514. Preferably, a greater number of rows of similar configured domes/balls 561 are positioned on lower portion 512. When the collar 567 is slid in the direction of the arrow of FIG. 11A, the ramp 568 of arm 562 is engaged to cam arm 562 downwardly against its normal bias so the domes 569 (engagement structure) move from a non-engaged to an engaged position to engage the dome engagement structure on lower portion 512. Note the domes 569 are preferably configured and dimensioned to fit within the space between domes 561. This is shown in FIG. 11A.

A second pivoting arm (not shown) identical to pivoting arm 562 is provided on the other side of the outer frame portion 514 to frictionally engage a corresponding series of projections, e.g. domes/balls (not shown) identical to domes 561 upon movement of a second collar (not shown) identical to collar 567. Thus, as in the embodiments of FIGS. 6 and 8, the engagement structure provides retention of the frame portions in the select spread positions. Such engagement is retained by the collars.

It should be appreciated that a different number of balls/domes can be provided in order to achieve retention of the dome structures.

In the alternate embodiment of FIG. 12, the locking mechanism, designated generally by reference numeral 660, is shown which can be utilized with the access ports of FIGS. 1 and 1A. That is, the access port of FIG. 12 is identical to the access port 100 of FIG. 1 except for the locking mechanism. More specifically, locking mechanism 660 has a plurality of transversely extending bars 664 on the upper surface of lower portion 612 and a plurality of similar transverse bars 664 on the lower surface 665 of the pivoting locking arm 662. Although the arm 662 is shown integral, as in the other embodiments disclosed herein, it could alternatively be a separate component attached to the upper portion. Only a few of the bars are labeled for clarity.

In the illustrated embodiment, two bars 669 are positioned on pivoting arm 662 of frame portion 614. Preferably, a greater number of bars 664 are positioned on lower portion 612. When the collar 667 is slid in the direction of the arrow of FIG. 13A, the ramp 668 of arm 662 is engaged to cam arm 662 downwardly against its normal bias so the bars 669 (engagement structure) move from a non-engaged to an engaged position to engage bar engagement structure on lower portion 612. That is, the bars 669 are moved into the space between bars 664 as shown in FIG. 13A.

A second pivoting arm (not shown) identical to pivoting arm 662 is provided on the other side of the upper frame portion 614 to engage bars (not shown) identical to bars 664 positioned on the other side of lower frame portion 612 upon movement of a second collar (not shown) identical to collar 667.

The use of the access port will now be described in conjunction with the embodiment of FIG. 1, it being understood that the embodiment of FIG. 1A would work in a similar fashion (except for the simultaneous movement of the collars by the bridge) and the other locking mechanisms of FIGS. 6-13 would also function in a similar fashion to FIG. 1, the difference being the differing engagement structures of the lower surface of the pivoting arm and the upper surface of the lower outer frame portion.

The use of the access port is described for thoracic surgery, it being understood that it can be utilized in other minimally invasive procedures.

Initially, an opening, or incision, is made in the patient's outer tissue wall of the thoracic body cavity by conventional means. The incision is made between adjacent ribs "R" (FIG. 2), extending along the intercostal space, and is relatively narrow and elongated.

For insertion through the incision, the inner member 150 is bent or reconfigured to reduce its transverse dimension for insertion through the patient's incision and into the body cavity. Note different sizes of access ports can also be used to accommodate different patients.

With access port 100 in the placement position, the inner frame (member) 150 is positioned within the body cavity adjacent the inner portion of the incision, flexible membrane 170 extends through the incision to outside the patient's body, and outer frame (member) 110 rests on the patient's skin. The outer frame 110 can now be expanded (see FIG. 2). Note the longitudinal axis of the inner frame 150 is substantially parallel to a long axis of the incision and the longitudinal axis of outer frame 110 is substantially transverse to a long axis of the incision, the longitudinal axis defining the length of the respective frame which exceeds its width.

In the initial position of access port 100, flexible member, e.g. membrane 170, defines a funnel shape with outer frame 110 retaining proximal end 172 of flexible membrane 170 while distal end 174 of flexible membrane 170 defines a smaller diameter due to the engagement of distal end 174 with the smaller inner frame 150. That is, since the width and length of outer member 110 is greater than the width and length of inner member 150 to which the membrane 170 is attached at its distal end, a funnel shape is formed. In this initial position, lip 152 of inner member 150, is configured to seat a rib "R" of a patient therein to protect the rib "R," the intercostal nerve, and surrounding tissue. That is, lip 152 extends upwardly into the opening in tissue adjacent the ribs "R," i.e., within the thoracic cavity "T". Additional cushioning (not shown) may be provided to provide further protection to ribs "R" and to surrounding tissue. Outward flexion of flexible membrane 170 expands the intercostal space, thus maximizing passageway 190, and giving access port 100 the maximum length.

In use, to spread the first and second portions or sections 112 and 114 of outer frame 110 to stretch (radially tension) the flexible membrane 170 to retract tissue adjacent the ribs and incision and widen the incision passageway 190 for instrumentation, the end wall 115 of the second portion 114 and the end wall 113 of the first portion 112 are grasped by the surgeon and pulled away from each other, thereby expanding the distance between end walls 113 and 115. Note the tissue is spread transverse to the long axis of the incision. When the desired spread position, i.e. desired tissue retraction, is achieved, the surgeon slides locking collar 167 along frame 110 and over the pivoting arm 162 (see FIG. 4A) and locking collar 167a along frame 110 and over pivoting arm 162a, forcing the arms 162, 162a to pivot toward the first (lower) portion 112 such that the engagement surfaces are moved from a non-engaged position to an engaged position to lock (secure) the upper and lower portions 114, 112 in the select position. This engagement of the engagement structures enhances the securement of the two portions 112 and 114 by limiting slippage as the locking collars 167, 167a clamp the two portions 112, 114 against movement. (In the embodiment of FIG. 1A the surgeon can slide the bridge 292 to move both locking collars together as described above). As noted above, the locking collars of the other embodiments described herein function in a similar manner to clamp the upper frame portions against movement as the various engagement structures are engaged.

With access port 100 secured in the desired expanded position, surgical instrumentation may be inserted through opening 170, passageway 190, and opening 155 to perform the surgical procedure within the body cavity. The low-profile configuration of access port 100, along the external surface of tissue, allows for greater access to the thoracic cavity "T" and for greater manipulation of instrumentation disposed through passageway 190.

Note that in the embodiments described herein, the engagement structures can be configured to provide sufficient frictional engagement to restrict movement, with the collars securely locking the engagement structures, or alternatively, configured to slightly frictionally engage with a slight retention force and mostly to prevent slippage, relying mainly on the collars to restrict any movement.

Upon completion of the surgical procedure, locking collars 167, 167a are moved toward their original position, to release the pivoting arms 162 and 162a to allow them to move to their unlocked non-engaged position, thereby allowing the frame portions 110, 112 to be moved toward each other toward their initial position to untension flexible membrane 170. Next, the surgeon may grasp inner member 150 to fold or reconfigure it to reduce its transverse dimension to remove it from the body cavity and through the incision.

As will be appreciated, access port 100 is easily inserted, manipulated, and removed from a patient's body. Further, the access port 100 is minimally intrusive, flexible to conform to a patient's anatomy, and provides good visibility into the thoracic cavity "T" (FIG. 3). Additionally, the low-profile configuration of access port 100 is particularly advantageous, for example, in the removal, or retrieval, of tissue specimens from within the body.

The flexible membrane 170 may be coated with a lubricant, or gel, to aid in the insertion and removal of surgical instrumentation and/or tissue specimens from access port 100.

In the embodiments described herein, the pivoting arms move from a "non-engaged" to an "engaged" position by the sliding collar. It should be appreciated that such "non-engaged" position can include a "non-locking" position wherein the engagement structures are in partial engagement, e.g. in contact, but not yet in full engagement, and then they would be moved by the collars to an engaged retention position where movement would be restricted.

Although described for use in thoracic procedures, it should also be understood that the access ports described herein can be used in other minimally invasive surgical procedures.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described, except as indicated by the appended claims.

What is claimed is:

1. A method of accessing an internal cavity of a patient comprising:
    forming an opening in a patient's tissue;
    providing an access assembly including:
        an outer member positionable outside the patient and defining an opening therein dimensioned to receive a surgical instrument, the outer member including first and second portions, the first and second portions being relatively movable to adjust a dimension of the opening;
        an inner member configured and dimensioned for insertion through the opening in the patient's tissue;
        a flexible member extending between the inner member and the outer member and operatively associated with the outer member, the flexible member defining a passageway configured and dimensioned to receive the surgical instrument, wherein relative movement between the first and second portions of the outer member adjusts tension on the flexible member; and
        a first locking member including a first arm;
    inserting the inner member into the opening in the patient's tissue such that the inner member is passed into an intercostal space defined between the patient's adjacent ribs such that the flexible member extends proximally through the opening in the patient's tissue;
    enlarging the opening in the patient's tissue and the passageway through the flexible member by effecting relative movement between the first and second portions of the outer member; and
    subsequently actuating the first locking member to lock the outer member in one of a plurality of select expanded positions by embedding a tip of the first arm in a soft material of the outer member.

2. The method according to claim 1, further including passing the surgical instrument and/or a tissue specimen through the passageway extending through the flexible member and the opening in the patient's tissue.

3. The method of claim 1, wherein inserting the inner member into the opening in the patient's tissue includes folding the inner member.

4. The method of claim 1, wherein actuating the first locking member includes sliding a first collar in relation to the outer member to embed the tip of the first arm in the soft material of the outer member.

5. The method of claim 4, wherein sliding the first collar in relation to the outer member includes contacting a ramped surface of the first arm with the first collar to cam the first arm towards the soft material of the outer member.

6. The method of claim 5, wherein providing the access assembly includes providing a second locking member including a second arm.

7. The method of claim 6 further including actuating the second locking member to lock the outer member in one of the plurality of select expanded positions by embedding a tip of the second arm in the soft material of the outer member.

8. The method of claim 7, wherein actuating the second locking member includes sliding a second collar in relation to the outer member to embed the tip of the second arm in the soft material of the outer member.

9. The method of claim 8, wherein sliding the second collar in relation to the outer member includes contacting a ramped surface of the second arm with the second collar to cam the second arm towards the soft material of the outer member.

10. A method of accessing an internal workspace comprising:
    inserting an access assembly into an opening in tissue such that an inner member of the access assembly is positioned beneath the tissue, an outer member of the access assembly is positioned above the tissue, and a flexible member connecting the inner and outer members extends through the opening in the tissue;

moving the outer member into an expanded configuration to enlarge the opening in the tissue by effecting relative movement between first and second portions of the outer member;

actuating a locking mechanism of the access assembly to lock the outer member in the expanded configuration by embedding a portion of the locking mechanism in a portion of the outer member; and introducing at least one surgical instrument into the internal workspace through a passageway defined by the flexible member.

11. The method of claim 10, wherein moving the outer member into the expanded configuration applies tension to the flexible member.

12. The method of claim 10, wherein actuating the locking mechanism includes pivoting a first arm of the locking mechanism towards the outer member.

13. The method of claim 12, wherein actuating the locking mechanism further includes embedding a tip of the first arm in a soft material of the outer member.

14. The method of claim 13, wherein actuating the locking mechanism includes sliding a first collar in relation to the outer member such that the first collar contacts a ramped surface of the first arm to cam the first arm towards the soft material of the outer member.

15. The method of claim 14, wherein actuating the locking mechanism further includes pivoting a second arm of the locking mechanism towards the outer member.

16. The method of claim 15, wherein actuating the locking mechanism further includes embedding a tip of the second arm in the soft material of the outer member.

17. The method of claim 16, wherein actuating the locking mechanism further includes sliding a second collar in relation to the outer member such that the second collar contacts a ramped surface of the second arm to cam the second arm towards the soft material of the outer member.

* * * * *